United States Patent
Filosa et al.

(10) Patent No.: US 9,505,255 B2
(45) Date of Patent: Nov. 29, 2016

(54) THERMAL IMAGING MEMBERS AND METHODS

(71) Applicant: ZINK IMAGING, INC., Bedford, MA (US)

(72) Inventors: Michael P Filosa, Medfield, MA (US); Stephen J. Telfer, Arlington, MA (US); John L Marshall, Lexington, MA (US); Richard M Allen, Norton, MA (US); John M Hardin, Hopkinton, MA (US)

( * ) Notice: Subject to any disclaimer, the term of this patent is extended or adjusted under 35 U.S.C. 154(b) by 0 days.

(21) Appl. No.: 14/276,395

(22) Filed: May 13, 2014

(65) Prior Publication Data

US 2015/0119237 A1 Apr. 30, 2015

Related U.S. Application Data

(63) Continuation of application No. 13/458,445, filed on Apr. 27, 2012, now Pat. No. 8,722,574, which is a continuation of application No. 12/940,709, filed on Nov. 5, 2010, now abandoned, which is a continuation of application No. 11/433,808, filed on May 12, 2006, now Pat. No. 7,829,497.

(60) Provisional application No. 60/680,088, filed on May 12, 2005, provisional application No. 60/680,212, filed on May 12, 2005.

(51) Int. Cl.
| | | |
|---|---|---|
| *B41M 5/327* | (2006.01) | |
| *B41M 5/333* | (2006.01) | |
| *C07D 493/10* | (2006.01) | |
| *C09B 11/24* | (2006.01) | |
| *B41M 5/337* | (2006.01) | |
| *C09B 67/48* | (2006.01) | |
| *C07D 493/20* | (2006.01) | |
| *B41M 5/382* | (2006.01) | |
| *B41M 5/385* | (2006.01) | |

(52) U.S. Cl.
CPC ......... *B41M 5/3275* (2013.01); *B41M 5/3375* (2013.01); *C07D 493/10* (2013.01); *C07D 493/20* (2013.01); *C09B 11/24* (2013.01); *C09B 67/0025* (2013.01); *B41M 5/3335* (2013.01); *B41M 5/385* (2013.01); *B41M 5/38235* (2013.01)

(58) Field of Classification Search
CPC ............ B41M 5/3275; B41M 3/3335; B41M 5/3375; C07D 493/10; C09B 11/24
USPC .......................... 503/200–226; 549/227, 265
See application file for complete search history.

(56) References Cited

FOREIGN PATENT DOCUMENTS

| EP | 1491590 | * 12/2004 | ............. C09B 11/12 |
|---|---|---|---|
| WO | WO 2004/078875 | * 9/2004 | |

* cited by examiner

*Primary Examiner* — Bruce H Hess
(74) *Attorney, Agent, or Firm* — Daniel Rose; Foley & Lardner LLP

(57) ABSTRACT

There are described thermal imaging members and thermal imaging methods utilizing unsymmetrical rhodamine compounds. The rhodamine color-forming compounds exhibit a first color when in a crystalline form and a second color, different from the first color, when in an amorphous form.

9 Claims, No Drawings

THERMAL IMAGING MEMBERS AND METHODS

REFERENCE TO RELATED APPLICATIONS

This application is a continuation of U.S. patent application Ser. No. 13/458,445, filed Apr. 27, 2012, which is a continuation of U.S. patent application Ser. No. 12/940,709, filed Nov. 5, 2010, which is a continuation of U.S. patent application Ser. No. 11/433,808, filed May 12, 2006, which claims the benefit of priority of provisional patent application Ser. Nos. 60/680,088 and 60/680,212, both filed May 12, 2005, the contents of which are incorporated herein by reference in their entireties.

This application is related to the following commonly assigned, United States patent applications and patents, the contents of which are incorporated herein by reference in their entireties:

U.S. Pat. No. 6,801,233 B2;
U.S. Pat. No. 6,906,735 B2;
U.S. Pat. No. 6,951,952 B2;
U.S. Pat. No. 7,008,759 B2;
U.S. patent application Ser. No. 10/806,749, filed Mar. 23, 2004, which is a division of U.S. Pat. No. 6,801,233 B2;
United States Patent Application Publication No. US2004/0176248 A1;
United States Patent Application Publication No. US2004/0204317 A1;
United States Patent Application Publication No. US2004/0171817 A1;
U. S. patent application Ser. No. (11/400,735; filed on Apr. 6, 2006
U. S. patent application Ser. No. (11/400,734; filed on Apr. 6, 2006); and
U. S. patent application Ser. No. (11/433,810; filed on even date herewith, Express Mail No.: EV 669114318 US.

FIELD OF THE INVENTION

This invention relates to thermal imaging members and methods and, more particularly, to such imaging members and methods in which there are utilized a color-former that exhibits one color in the crystalline form and a second, different color in the liquid, or amorphous, form.

BACKGROUND OF THE INVENTION

The development of thermal print heads (linear arrays of individually-addressable heating elements) has led to the development of a wide variety of thermally-sensitive imaging materials. In some of these, known as "thermal transfer" systems, heat is used to move colored material from a donor sheet to a receiver sheet. Alternatively, heat may be used to convert a colorless coating on a single sheet into a colored image, in a process known as "direct thermal" imaging. Direct thermal imaging has the advantage over thermal transfer of the simplicity of a single sheet. On the other hand, unless a fixing step is incorporated, direct thermal systems are still sensitive to heat after thermal printing. If a stable image is needed from an unfixed direct thermal system, the temperature for coloration must be higher than any temperature that the image is likely to encounter during normal use. A problem arises in that the higher the temperature for coloration, the less sensitive the imaging member will be when printed with the thermal print head. High sensitivity is important for maximum speed of printing, for maximizing the longevity of the print head, and for energy conservation in mobile, battery-powered printers. As described in more detail below, maximizing sensitivity while maintaining stability is more easily achieved if the temperature of coloration of a direct thermal medium is substantially independent of the heating time.

Thermal print heads address one line of the image at a time. For reasonable printing times, each line of the image is heated for about ten milliseconds or less. Storage of the medium (prior to printing or in the form of the final image) may need to be for years, however. Thus, for high imaging sensitivity, a high degree of coloration is required in a short time of heating, while for good stability a low degree of coloration is required for a long time of heating.

Most chemical reactions speed up with increasing temperature. Therefore, the temperature required for coloration in the short heating time available from a thermal print head will normally be higher than the temperature needed to cause coloration during the long storage time. Reversing this order of temperatures would be a very difficult task, but maintaining a substantially time-interval-independent temperature of coloration, such that the temperatures required for coloration over both long and short time intervals are substantially the same, is a goal that is achieved by the present invention.

There are other reasons why a time-interval-independent coloration temperature may be desirable. It may, for example, be required to perform a second thermal step, requiring a relatively long time of heating, after printing. An example of such a step would be thermal lamination of an image. The temperature of coloration of the imaging material during the time required for thermal lamination must be higher than the lamination temperature (otherwise the material would become colorized during lamination). It would be preferred that the imaging temperature be higher than the lamination temperature by as small a margin as possible. This would be the case for time-interval-independent temperature of coloration.

Finally, the imaging system may comprise more than one color-forming layer and be designed to be printed with a single thermal print-head, as described in the above-mentioned U.S. Pat. No. 6,801,233 B2. In one embodiment of the imaging system, the topmost color-forming layer forms color in a relatively short time at a relatively high temperature, while the lower layer or layers form color in a relatively long time at a relatively low temperature. An ideal topmost layer for this type of direct thermal imaging system would have time-interval-independent temperature of coloration.

Prior art direct thermal imaging systems have used several different chemical mechanisms to produce a change in color. Some have employed compounds that are intrinsically unstable, and which decompose to form a visible color when heated. Such color changes may involve a unimolecular chemical reaction. This reaction may cause color to be formed from a colorless precursor, the color of a colored material to change, or a colored material to bleach. The rate of the reaction is accelerated by heat. For example, U.S. Pat. No. 3,488,705 discloses thermally unstable organic acid salts of triarylmethane dyes that are decomposed and bleached upon heating. U.S. Pat. No. 3,745,009 reissued as U.S. Reissue Pat. No. 29,168 and U.S. Pat. No. 3,832,212 disclose heat-sensitive compounds for thermography containing a heterocyclic nitrogen atom substituted with an —OR group, for example, a carbonate group, that decolorize by undergoing homolytic or heterolytic cleavage of the nitrogen-oxygen bond upon heating to produce an RO+ ion or RO' radical and a dye base or dye radical which may in part fragment further. U.S. Pat. No. 4,380,629 discloses styryl-like compounds that undergo coloration or bleaching, reversibly or irreversibly, via ring-opening and ring-closing in response to activating energies. U.S. Pat. No. 4,720,449 describes an intramolecular acylation reaction that converts a colorless molecule to a colored form. U.S. Pat. No.

4,243,052 describes pyrolysis of a mixed carbonate of a quinophthalone precursor that may be used to form a dye. U.S. Pat. No. 4,602,263 describes a thermally-removable protecting group that may be used to reveal a dye or to change the color of a dye. U.S. Pat. No. 5,350,870 describes an intramolecular acylation reaction that may be used to induce a color change. A further example of a unimolecular color-forming reaction is described in "New Thermo-Response Dyes: Coloration by the Claisen Rearrangement and Intramolecular Acid-Base Reaction", Masahiko Inouye, Kikuo Tsuchiya, and Teijiro Kitao, Angew. Chem. Int. Ed. Engl., 31, pp. 204-5 (1992).

In all of the above-mentioned examples, control of the chemical reaction is achieved through the change in rate that occurs with changing temperature. Thermally-induced changes in rates of chemical reactions in the absence of phase changes may often be approximated by the Arrhenius equation, in which the rate constant increases exponentially as the reciprocal of absolute temperature decreases (i.e., as temperature increases). The slope of the straight line relating the logarithm of the rate constant to the reciprocal of the absolute temperature is proportional to the so-called "activation energy". The prior art compounds described above are coated in an amorphous state prior to imaging, and thus no change in phase is expected or described as occurring between room temperature and the imaging temperature. Thus, as employed in the prior art, these compounds exhibit strongly time-interval-dependent coloration temperatures. Some of these prior art compounds are described as having been isolated in crystalline form. Nevertheless, in no case is there mentioned in this prior art any change in activation energy of the color-forming reaction that may occur when crystals of the compounds are melted.

Other prior art thermal imaging media depend upon melting to trigger image formation. Typically, two or more chemical compounds that react together to produce a color change are coated onto a substrate in such a way that they are segregated from one another, for example, as dispersions of small crystals. Melting, either of the compounds themselves or of an additional fusible vehicle, brings them into contact with one another and causes a visible image to be formed. For example, a colorless dye precursor may form color upon heat-induced contact with a reagent. This reagent may be a Bronsted acid, as described in "Imaging Processes and Materials", Neblette's Eighth Edition, J. Sturge, V. Walworth, A. Shepp, Eds., Van Nostrand Reinhold, 1989, pp. 274-275, or a Lewis acid, as described for example in U.S. Pat. No. 4,636,819. Suitable dye precursors for use with acidic reagents are described, for example, in U.S. Pat. No. 2,417,897, South African Patent 68-00170, South African Patent 68-00323 and Ger. Offenlegungschrift 2,259,409. Further examples of such dyes may be found in "Synthesis and Properties of Phthalide-type Color Formers", by Ina Fletcher and Rudolf Zink, in "Chemistry and Applications of Leuco Dyes", Muthyala Ed., Plenum Press, New York, 1997. The acidic material may for example be a phenol derivative or an aromatic carboxylic acid derivative. Such thermal imaging materials and various combinations thereof are now well known, and various methods of preparing heat-sensitive recording elements employing these materials also are well known and have been described, for example, in U.S. Pat. Nos. 3,539,375, 4,401,717 and 4,415,633.

Prior art systems in which at least two separate components are mixed following a melting transition suffer from the drawback that the temperature required to form an image in a very short time interval by a thermal print-head may be substantially higher than the temperature required to colorize the medium during longer periods of heating. This difference is caused by the change in the rate of the diffusion needed to mix the molten components together, which may become limiting when heat is applied for very short periods. The temperature may need to be raised well above the melting points of the individual components to overcome this slow rate of diffusion. Diffusion rates may not be limiting during long periods of heating, however, and the temperature at which coloration takes place in these cases may actually be less than the melting point of either individual component, occurring at the eutectic melting point of the mixture of crystalline materials.

U.S. patent application Ser. No. 10/789,648, filed Feb. 27, 2004 (United States Patent Application Publication No. US2004/0176248 A1), and assigned to the same assignee as the present application, is directed to a thermal imaging method wherein a dye is converted from one form in which the dye has one color to another form in which the dye has a second color, e.g., from colorless to colored.

Japanese Published Application No. 9-241553 discloses inkjet recording inks containing certain asymmetrical rhodamine dyes. U.S. Pat. No. 4,390,616 discloses thermal imaging members and methods utilizing certain rhodamine dyes.

As the state of the imaging art advances and efforts are made to provide new imaging systems that can meet new performance, requirements, it would be advantageous to have thermal imaging systems which utilize yet another class of dyes.

SUMMARY OF THE INVENTION

It is therefore an object of this invention to provide novel thermal imaging members and methods.

Another object of the invention is to provide such thermal imaging members and methods that utilize a color-former that exhibits different colors when in the crystalline form than when in the amorphous form.

Yet another object of the invention is to provide imaging members and methods that utilize certain rhodamine color-formers.

According to one aspect of the invention there are provided novel thermal imaging members and methods that utilize certain rhodamine color-forming compounds that exhibit a first color when in a crystalline form and a second color, different from the first color, when in an amorphous form.

In one embodiment of the invention there are provided novel thermal imaging members and methods that utilize compounds that are represented by formula I

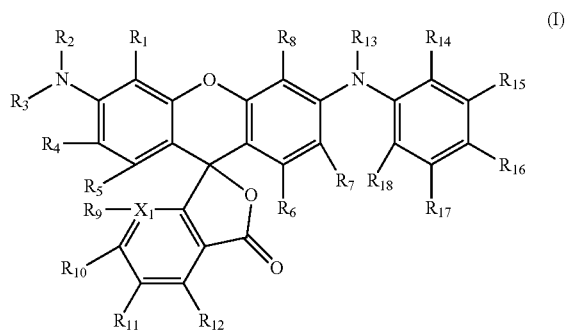

wherein: $R_1$, $R_3$, $R_4$, $R_5$, $R_6$, $R_7$, $R_8$ and $R_{14}$ are each independently selected from the group consisting of hydrogen, substituted or unsubstituted alkyl, preferably having from 1 to 18 carbon atoms, alkenyl or substituted alkenyl, preferably having from 1 to 18 carbon atoms, heterocycloalkyl, substituted heterocycloalkyl, alkoxy, substituted alkoxy, substituted carbonyl, acylamino, halogen, aryl, substituted aryl, heteroaryl and substituted heteroaryl;

$R_2$ is selected from the group consisting of hydrogen, alkyl or substituted alkyl, preferably having from 1 to 18 carbon atoms, alkenyl or substituted alkenyl, preferably having from 1 to 18 carbon atoms, heterocycloalkyl and substituted heterocycloalkyl; or $R_2$ and $R_3$ taken together with the nitrogen atom to which they are attached can form a substituted or unsubstituted saturated heterocyclic ring system, such as, for example, substituted and unsubstituted morpholines, pyrrolidines, and piperidines;

$R_9$ is absent or selected from the group consisting of hydrogen, substituted or unsubstituted alkyl, preferably having from 1 to 18 carbon atoms, substituted or unsubstituted alkenyl, preferably having from 1 to 18 carbon atoms, heterocycloalkyl, substituted heterocycloalkyl, alkoxy, substituted alkoxy, substituted carbonyl, halogen, aryl, substituted aryl, heteroaryl, substituted heteroaryl, amino, substituted amino, alkylamino, substituted alkylamino, arylamino and substituted arylamino;

$R_{10}$, $R_{11}$ and $R_{12}$ are each independently selected from the group consisting of hydrogen, substituted or unsubstituted alkyl, preferably having from 1 to 18 carbon atoms, substituted or unsubstituted alkenyl, preferably having from 1 to 18 carbon atoms, heterocycloalkyl, substituted heterocycloalkyl, alkoxy, substituted alkoxy, substituted carbonyl, halogen, aryl, substituted aryl, heteroaryl, substituted heteroaryl, amino, substituted amino, alkylamino, substituted alkylamino, arylamino and substituted arylamino;

$R_{13}$ is selected from the group consisting of hydrogen, substituted or unsubstituted alkyl, preferably having from 1 to 18 carbon atoms, substituted or unsubstituted alkenyl, preferably having from 1 to 18 carbon atoms, heterocycloalkyl and substituted heterocycloalkyl;

$R_{14}$ is selected from the group consisting of hydrogen, substituted or unsubstituted alkyl, preferably having from 1 to 18 carbon atoms, substituted or unsubstituted alkenyl, preferably having from 1 to 18 carbon atoms, heterocycloalkyl and substituted heterocycloalkyl; or $R_{13}$ and $R_{14}$ taken together with the atoms to which they are attached can form a 5- or 6-membered heterocyclic ring such as, for example, indoline or tetrahydroquinoline;

$R_{15}$, $R_{16}$, $R_{17}$ and $R_{18}$ are each independently selected from the group consisting of hydrogen, substituted or unsubstituted alkyl, preferably having from 1 to 18 carbon atoms, substituted or unsubstituted alkenyl, preferably having from 1 to 18 carbon atoms, heterocycloalkyl, substituted heterocycloalkyl, alkoxy, substituted alkoxy, substituted carbonyl, halogen, aryl, substituted aryl, heteroaryl, substituted heteroaryl, amino, substituted amino, alkylamino, substituted alkylamino, arylamino and substituted arylamino;

$X_1$ is carbon or nitrogen; and at least one of $R_2$ and $R_{13}$ is hydrogen.

The substituents are preferably chosen to minimize the water solubility of the compounds and facilitate the formation of a colorless form in non-polar, non-protic solvents. In turn, the colorless lactone form of the compounds must be capable of melting to form the colored form.

A preferred group of compounds for use according to the invention are those represented by formula I wherein $R_2$ and $R_3$ taken together form a pyrrolidine ring, $R_{10}$, $R_{11}$ and $R_{13}$ each is hydrogen, $X_1$ is carbon and $R_1$, $R_4$, $R_5$, $R_6$, $R_7$, $R_8$, $R_9$, $R_{12}$, $R_{14}$, $R_{15}$, $R_{16}$, $R_{17}$ and $R_{18}$ are as previously described with respect to formula I.

A second preferred group of compounds for use according to the invention are those represented by formula I wherein $R_2$ is hydrogen, $R_3$ is alkyl, $R_{10}$ and $R_{11}$ are each halogen, $R_{13}$ is alkyl, $X_1$ is carbon and $R_1$, $R_4$, $R_5$, $R_6$, $R_7$, $R_8$, $R_9$, $R_{12}$, $R_{14}$, $R_{15}$, $R_{16}$, $R_{17}$ and $R_{18}$ are as described with respect to formula I.

A third preferred group of compounds for use according to the invention are those represented by formula I wherein $R_2$ is hydrogen, $R_3$ is aryl or substituted aryl, $R_{13}$ and $R_{14}$ are alkyl and $R_1$, $R_4$, $R_5$, $R_6$, $R_7$, $R_8$, $R_9$, $R_{10}$, $R_{11}$, $R_{12}$, $R_{15}$, $R_{16}$, $R_{17}$, $R_{19}$ and $X_1$ are as described with respect to formula I.

Particularly preferred rhodamine compounds for use according to the invention are those represented by formula I in which $R_1$, $R_4$, $R_5$, $R_6$, $R_7$, $R_8$, $R_9$ and $R_{12}$ are each hydrogen; $R_2$ is hydrogen or alkyl having from 1-18 carbon atoms, $R_3$ is alkyl having from 1-18 carbon atoms, aryl or substituted aryl, or $R_2$ and $R_3$ taken together with the nitrogen atom to which they are attached form a pyrrolidine ring; $R_{10}$ and $R_{11}$ are each independently hydrogen or halogen; $R_{13}$ is hydrogen or alkyl, preferably having from 1-18 carbon atoms, $R_{14}$ is hydrogen or alkyl having from 1-18 carbon atoms, $X_1$ is carbon and $R_{15}$, $R_{16}$, $R_{17}$ and $R_{18}$ are each independently hydrogen, alkyl having from 1-18 carbon atoms, or halogen.

The conversion from the crystalline form to the amorphous form in accordance with the thermal imaging members and thermal imaging methods of the invention is carried out by applying heat to the compounds. In the thermal imaging methods of the invention thermal energy may be applied to the thermal imaging members by any of the techniques known in thermal imaging such as from a thermal print head, a laser, a heated stylus, etc.

In another embodiment, one or more thermal solvents, which are crystalline materials, can be incorporated in the thermal imaging member. The crystalline thermal solvent(s), upon being heated, melt and dissolve or liquefy, and thereby convert, at least partially, the crystalline color-forming material to the amorphous form to form the image.

When converted to the colored form the compounds of formula I have the open form illustrated by formula II (for the case where $R_2$ in formula I is hydrogen)

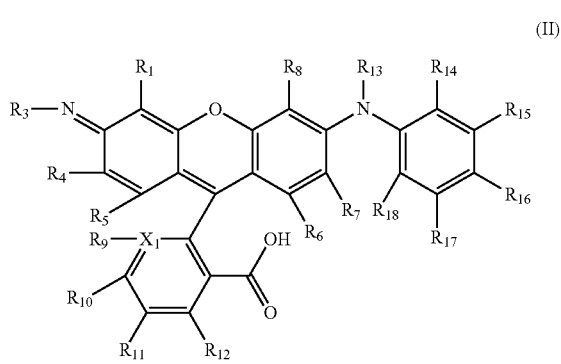

(II)

or formula III (for the case where $R_{13}$ in formula I is hydrogen).

(III)

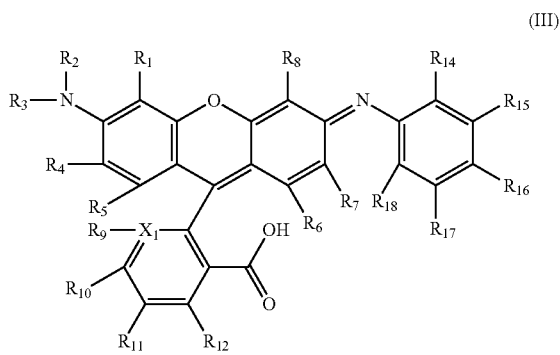

wherein $R_1$, $R_3$-$R_{18}$, and $X_1$ are as defined above with respect to formula I.

According to the invention the compounds of formula I may be incorporated in any thermal imaging members and used in any thermal imaging methods including thermal transfer imaging members and methods and direct thermal imaging members and methods. The thermal imaging members of the invention may be for use in thermal transfer imaging such as is disclosed in U.S. Pat. No. 6,537,410 B2. Conventional methods for color thermal imaging such as thermal wax transfer printing and dye-diffusion thermal transfer typically involve the use of separate donor and receiver materials. The donor material typically has a colored image-forming material, or a color-forming imaging material, coated on a surface of a substrate and the image-forming material or the color-forming imaging material is transferred thermally to the receiver material. In order to make multicolor images, a donor material with successive patches of differently-colored, or different color-forming, material may be used. In the case of printers having either interchangeable cassettes or more than one thermal head, different monochrome donor ribbons are utilized and multiple color separations are made and deposited successively above one another.

The thermal imaging members according to the invention may be for use in direct thermal printing methods and such thermal imaging members include all the color-forming reagents necessary to form an image in the member. Such direct thermal imaging members according to the invention may be used in any direct thermal imaging method such as, for example, disclosed in U.S. Pat. No. 6,801,233 B2.

Thermal imaging members according to the invention generally comprise a substrate carrying at least one image-forming layer including a compound according to formula I in the crystalline form, which can be converted, at least partially to an amorphous form, the amorphous form having intrinsically a different color from the crystalline form. The imaging member may be monochromatic, in which an image-forming layer includes at least one compound of formula I, or polychromatic. Multicolor direct thermal imaging members include at least two, and preferably three, image-forming layers and the temperature at which an image is formed in at least one of the image-forming layers is preferably time-interval-independent. Preferred imaging members according to the invention are direct multicolor thermal imaging members.

Any suitable thermal solvents may be incorporated in the thermal imaging members of the invention. Suitable thermal solvents include, for example, alkanols containing at least about 12 carbon atoms, alkanediols containing at least about 12 carbon atoms, monocarboxylic acids containing at least about 12 carbon atoms, esters and amides of such acids, aryl sulfonamides and hydroxyalkyl-substituted arenes.

Specific preferred thermal solvents include: tetradecan-1-ol, hexadecan-1-ol, octadecan-1-ol, dodecane-1,2-diol, hexadecane-1,16-diol, myristic acid, palmitic acid, stearic acid, methyl docosanoate, 1,4-bis(hydroxymethyl)benzene, and p-toluenesulfonamide.

Particularly preferred thermal solvents are diaryl sulfones such as diphenylsulfone, 4,4'-dimethyldiphenylsulfone, phenyl p-tolylsulfone and 4,4'-dichlorodiphenylsulfone.

It is possible that the dissolution of the compounds of formula I by a thermal solvent may lead to an amorphous form (in which the compound is dissolved in the amorphous thermal solvent) in which the proportion of the open, colored form is different from the proportion that would be present in the amorphous form resulting from melting the compound of formula I alone (i.e., without interaction with the thermal solvent). In particular, the proportion of the open, colored form of the compound in the amorphous material may be enhanced by use of hydrogen-bonding or acidic thermal solvents. Materials that increase the proportion of the color-forming material that is in the open, colored form are hereinafter referred to as "developers". It is possible that the same compound may serve the function of thermal solvent and developer. Preferred developers include phenols such as 2,2'-methylenebis(6-tert-butyl-4-methylphenol), 2,2'-methylenebis(6-tert-Butyl-4-Ethyl-Phenol), 2,2'-ethylidenebis(4,6-di-tert-butylphenol), bis[2-hydroxy-5-methyl-3-(1-methylcyclohexyl)phenyl]-methane, 1,3,5-tris(2,6-dimethyl-3-hydroxy-4-tert-butylbenzyl) isocyanurate, 2,6-bis[[3-(1,1-dimethylethyl)-2-hydroxy-5-methylphenyl]methyl]-4-methyl-phenol, 2,2'-butylidenebis[6-(1,1-dimethylethyl)-4-methyl-phenol, 2,2'-(3,5,5-trimethylhexylidene)bis[4,6-dimethyl-phenol], 2,2'-methylenebis[4,6-bis(1,1-dimethylethyl)-phenol, 2,2'-(2-methylpropylidene)bis[4,6-dimethyl-phenol], 1,1,3-tris(2-methyl-4-hydroxy-5-t-butylphenyl)butane, tris(3,5-di-t-butyl-4-hydroxybenzyl) isocyanurate, 2,2'-thiobis(4-tert-octylphenol), and 3-tert-butyl-4-hydroxy-5-methylphenyl sulfide.

In order for the image formed by the amorphous color-former to be stable against recrystallization back to the crystalline form, preferably the glass transition temperature ($T_g$) of the amorphous mixture of the color-former and any thermal solvent should be higher than any temperature that the final image must survive. Typically, it is preferred that the $T_g$ of the amorphous, colored material be at least about 50° C., and ideally above about 60° C. In order to ensure that the $T_g$ is sufficiently high for a stable image to be formed, materials having a high $T_g$ may be added to the color-forming composition. Such materials, hereinafter referred to as "stabilizers", when dissolved in the amorphous mixture of color-former, optional thermal solvent, and optional developer, serve to increase the thermal stability of the image.

Preferred stabilizers have a $T_g$ that is at least about 60° C., and preferably above about 80° C. Examples of such stabilizers are the aforementioned 1,3,5-tris(2,6-dimethyl-3-hydroxy-4-tert-butylbenzyl) isocyanurate ($T_g$ 123° C.) and 1,1,3-tris(2-methyl-4-hydroxy-5-t-butylphenyl)butane ($T_g$ 101° C.). It will be clear that the stabilizer molecule may also serve as a thermal solvent or as a developer.

For example, the color-forming material may itself have a melting temperature above the desired temperature for imaging, and a $T_g$ (in the amorphous form) of about 60° C. In order to produce a color-forming composition melting at the desired temperature, it may be combined with a thermal solvent (for example, a diaryl sulfone) that melts at the desired temperature for imaging. The combination of thermal solvent and color-forming material may, however, have a $T_g$ that is substantially lower than 60° C., rendering the (amorphous) image unstable. In this case, a stabilizer such as 1,3,5-tris(2,6-dimethyl-3-hydroxy-4-tert-butylbenzyl) isocyanurate may be added, to raise the $T_g$ of the amorphous material. In addition, there may be provided a developer, for example, a phenolic compound such as 2,2'-ethylidenebis (4,6-di-tert-butylphenol), in order to increase the proportion of the color-forming material that is in the colored form in the amorphous phase.

Preferably the color-forming compound of the present invention, the (optional) thermal solvent, the (optional) developer and the (optional) stabilizer are each predominantly in their crystalline forms prior to imaging. By "predominantly" is meant at least about 50%. During imaging, at least one of these materials melts and an amorphous mixture of the materials is formed. The amorphous mixture is colored, whereas the crystalline starting materials are not.

compound may explore its whole conformational and isomeric space, and only a small proportion of the population of individual molecules of the compound may at any one time exhibit the particular conformation or isomeric form adopted in the crystal. Compounds of the present invention exhibit tautomerism in which at least one tautomeric form is colorless, and at least another tautomeric form is colored. The crystalline form of compounds of the present invention comprises predominantly the colorless tautomer.

In a first embodiment of the invention there are provided thermal imaging members and methods which utilize a compound whose colorless tautomer is represented by formula I as described above.

Specific representative compounds utilized according to the invention are those of formula I which are shown in Table I in which the substituents $R_1$, $R_4$, $R_5$, $R_6$, $R_7$, $R_8$, $R_9$, $R_{11}$, $R_{15}$, $R_{17}$, $R_{18}$ are all hydrogen, $X_1$ is carbon and $R_2$, $R_3$, $R_{10}$, $R_{11}$, $R_{13}$, $R_{14}$ and $R_{16}$ are as shown:

TABLE I

| DYE | $R_2$ | $R_3$ | $R_{10}$ | $R_{11}$ | $R_{13}$ | $R_{14}$ | $R_{16}$ | M.P. | λmax |
|---|---|---|---|---|---|---|---|---|---|
| I | n-C10H21 | H | H | H | -(CH$_2$)$_3$— | | H | 124 | 570 |
| II | 2-EtPh | H | H | H | C8H17 | C2H5 | H | 144 | 548 |
| III | Ph | H | H | H | C4H9 | H | H | 172 | 552 |
| IV | 2-MePh | H | H | H | C8H17 | CH3 | H | 152 | 548 |
| V | 2-MePh | H | H | H | C6H13 | CH3 | H | 199 | 548 |
| VI | 2-MePh | H | H | H | C4H9 | H | H | 184 | 550 |
| VII | Cyclohexyl | H | H | H | C2H5 | H | H | 212 | 544 |
| VIII | Adamantyl | H | H | H | C2H5 | H | H | 240 | 544 |
| IX | Cyclohexyl | H | Cl | Cl | C4H9 | H | H | 193 | 554 |
| X | Adamantyl | H | Cl | Cl | C4H9 | H | H | 252 | 554 |
| XI | Cyclohexyl | H | Cl | Cl | C8H17 | H | H | 162 | 554 |
| XII | -(CH$_2$)$_4$— | | H | H | H | CH3 | H | 268 | 556 |
| XIII | -(CH$_2$)$_4$— | | H | H | H | CH3 | 4-F | 272 | 552 |
| XIV | -(CH$_2$)$_3$CHCH$_3$— | | H | H | H | CH3 | 4-F | 228 | 552 |

It is possible that one of the components in the amorphous, colored mixture may recrystallize after the image has been formed. It is desirable that such recrystallization not change the color of the image. In the case that a color-former, thermal solvent, developer and stabilizer are used, the thermal solvent may typically recrystallize without greatly affecting the color of the image.

Preferred thermal imaging members according to the invention are direct thermal imaging members, particularly those having the structures described in commonly assigned U.S. Pat. No. 6,801,233 B2.

Other preferred thermal imaging members are those for use in thermal transfer imaging methods, particularly those having the structures described in commonly assigned U.S. Pat. No. 6,537,410.

Further preferred thermal imaging members are thermal transfer imaging members having the structures described in commonly assigned U.S. Pat. No. 6,054,246.

DETAILED DESCRIPTION OF THE INVENTION

Compounds in the crystalline state commonly have properties, including color, that are very different from those of the same compounds in an amorphous form. In a crystal, a molecule is typically held in a single conformation (or, more rarely, in a small number of conformations) by the packing forces of the lattice. Likewise, if a molecule can exist in more than one interconverting isomeric form, only one of such isomeric forms is commonly present in the crystalline state. In amorphous form or solution, on the other hand, the Compounds I and VII-XIV are novel compounds which are disclosed and claimed in co-pending U.S. patent application Ser. No., 11/433,810, filed on even date herewith, Express Mail No.: EV 669114318 US.

Definitions

The term "alkyl" as used herein refers to saturated straight-chain, branched-chain or cyclic hydrocarbon radicals. Examples of alkyl radicals include, but are not limited to, methyl, ethyl, propyl, isopropyl, n-butyl, tert-butyl, neopentyl, n-hexyl, cyclohexyl, n-octyl, n-decyl, n-dodecyl and n-hexadecyl radicals.

The term "alkenyl" as used herein refers to unsaturated straight-chain, branched-chain or cyclic hydrocarbon radicals. Examples of alkenyl radicals include, but are not limited to, allyl, butenyl, hexenyl and cyclohexenyl radicals.

The term "alkynyl" as used herein refers to unsaturated hydrocarbon radicals having at least one carbon-carbon triple bond. Representative alkynyl groups include, but are not limited to, ethynyl, 1-propynyl, 1-butynyl, isopentynyl, 1,3-hexadiynyl, n-hexynyl, 3-pentynyl, 1-hexen-3-ynyl and the like.

The terms "halo" and "halogen," as used herein, refer to an atom selected from fluorine, chlorine, bromine and iodine.

The term "aryl," as used herein, refers to a mono-, bicyclic or tricyclic carbocyclic ring system having one, two or three aromatic rings including, but not limited to, phenyl, naphthyl, anthryl, azulyl, tetrahydronaphthyl, indanyl, indenyl and the like.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl," as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "carbonyl" as used herein refers to a carbonyl group, attached to the parent molecular moiety through the carbon atom, this carbon atom also bearing a hydrogen atom, or in the case of a "substituted carbonyl" a substituent as described in the definition of "substituted" below.

The term "acyl" as used herein refers to groups containing a carbonyl moiety. Examples of acyl radicals include, but are not limited to, formyl, acetyl, propionyl, benzoyl and naphthoyl.

The term "alkoxy", as used herein, refers to a substituted or unsubstituted alkyl, alkenyl or heterocycloalkyl group, as previously defined, attached to the parent molecular moiety through an oxygen atom. Examples of alkoxy radicals include, but are not limited to, methoxy, ethoxy, propoxy, isopropoxy, n-butoxy, tert-butoxy, neopentyloxy and n-hexyloxy.

The term "aryloxy" as used herein refers to a substituted or unsubstituted aryl or heteroaryl group, as previously defined, attached to the parent molecular moiety through an oxygen atom. Examples of aryloxy include, but are not limited to, phenoxy, p-methylphenoxy, naphthoxy and the like.

The term "alkylamino", as used herein, refers to a substituted or unsubstituted alkyl, alkenyl or heterocycloalkyl group, as previously defined, attached to the parent molecular moiety through a nitrogen atom. Examples of alkylamino radicals include, but are not limited to, methylamino, ethylamino, hexylamino and dodecylamino.

The term "arylamino", as used herein, refers to a substituted or unsubstituted aryl or heteroaryl group, as previously defined, attached to the parent molecular moiety through a nitrogen atom.

The term "substituted" as used herein in phrases such as "substituted alkyl", "substituted alkenyl", "substituted aryl", "substituted heteroaryl", "substituted heterocycloalkyl", "substituted carbonyl", "substituted alkoxy", "substituted acyl", "substituted amino", "substituted aryloxy", and the like, refers to independent replacement of one or more of the hydrogen atoms on the substituted moiety with substituents independently selected from, but not limited to, alkyl, alkenyl, heterocycloalkyl, alkoxy, aryloxy, hydroxy, amino, alkylamino, arylamino, cyano, halo, mercapto, nitro, carbonyl, acyl, aryl and heteroaryl groups.

The term "substituted" as used herein in phrases such as "substituted nitrogen", "substituted oxygen" and "substituted sulfur" refers to nitrogen, oxygen or sulfur substituted with alkyl, aryl, or heteroaryl groups. Examples include, but are not limited to, alkyl and aryl ethers such as methoxy, ethoxy or phenoxy; alkyl or aryl thioethers such as thiomethoxy, thioethoxy and thiophenyl; alkyl or aryl amines such as dimethylamino, diethylamino, diphenylamino, phenylamino, and N-methyl-N-phenylamino.

According to the invention, there are utilized molecules exhibiting tautomerism in which at least one tautomeric form is colorless, and at least another tautomeric form is colored. Crystallization of the equilibrating mixture of the two tautomeric forms is carried out so as to produce colorless crystals. The solvent chosen to perform the crystallization will typically be one of such polarity (and other chemical properties, such as hydrogen-bonding ability) that the pure colorless crystal form is favored, either in the equilibrium between the colorless and colored forms in solution, or in having lower solubility in the solvent than the colored form. The choice of solvent is usually determined empirically for a particular mixture of tautomers.

Upon conversion of the pure crystalline colorless form to an amorphous form, the equilibrium between the two tautomers is re-established. The proportion of the amorphous material that is colored (i.e., the proportion that is in the colored tautomeric form) may vary, but is preferably at least about 10%.

The colored and colorless tautomeric forms of the molecules utilized according to the present invention should meet certain criteria for image quality and permanence. The colorless form, which is preferably the crystalline form, should have minimal visible absorption. It should be stable to light, heating below the melting point, humidity, and other environmental factors such as ozone, oxygen, nitrogen oxides, fingerprint oils, etc. These environmental factors are well known to those skilled in the imaging art. The colored, amorphous form should be stable also to the above mentioned conditions, and in addition should not recrystallize to the colorless form under normal handling conditions of the image. The colored form should have a spectral absorption appropriate for digital color rendition. Typically, the colored form should be yellow (blue-absorbing), magenta (green-absorbing), cyan (red absorbing), or black, without undue absorption in an unintended spectral region. For non-photographic applications, however, it may be required that the colored form not be one of the subtractive primary colors, but rather a particular spot color (for example, orange, blue, etc.).

The compounds used according to the invention may be prepared by synthetic processes which are known to those skilled in the art, particularly in view of the state of the art in organic synthetic processes, and the present disclosure and specific preparatory examples provided below herein.

Generally, symmetrical rhodamine dyes can be prepared in one step from 3',6'-dichlorofluorans by reacting two equivalents of an aromatic or aliphatic amine as described in U.S. Pat. No. 4,602,263, GB2311075 and DE81056. The unsymmetrical rhodamine dyes are then prepared by the selective monoalkylation of symmetrical rhodamines using sodium hydride in dimethyl sulfoxide as described in U.S. Pat. Nos. 4,602,263 and 4,826,976.

Alternatively, the unsymmetrical rhodamines can be prepared by use of an alternate synthetic pathway in which one equivalent of an N-alkylaniline is reacted selectively with the 3',6'-dichlorofluoran using aluminum chloride as a catalyst to produce 3'-chloro-6'-N-alkyl-N-arylfluorans. These products are isolated and purified prior to reacting with a second equivalent of an aromatic or aliphatic amine. Zinc chloride is used as the catalyst for the second addition. DE139727 describes the selective addition of anilines to 3',6'-dichlorofluorans to produce 3'-chloro-6'-arylaminofluorans using a mixture of zinc chloride and zinc oxide at 160° C.

Unsymmetrical rhodamines can also be made from 2-benzoyl benzoic acid derivatives by condensation with 3-arylamino phenols or 3-alkylamino phenols as described in *Chemistry and Applications of Leuco Dyes*, pp. 180-191 R. Muthyala, Ed., Plenum Press, New York and London, 1997 and also U.S. Pat. Nos. 4,390,616 and 4,436,920.

To optimize the chromophore, melting point, degree of coloration, light stability and solubility of the dyes of this application a variety of anilines, N-alkylanilines, aliphatic amines and dichlorofluorans are utilized.

The 3',6'-dichlorofluorans are synthesized from the corresponding fluoresceins using thionyl chloride and dimethylformamide in a variation of the method of Hurd described in the Journal of the Amer. Chemical Soc. 59, 112 (1937).

Careful recrystallization from solvent mixtures such as hexanes/acetone or hexanes/ethyl acetate produces colorless crystalline material which is preferred for use in thermal imaging members.

As described above, the thermal imaging members of the invention can be direct thermal imaging members wherein an image is formed in the member itself or they can be thermal transfer imaging members whereby image-forming material is transferred to an image-receiving member. The melting point of the molecules used in direct thermal imaging members of the present invention is preferably in the range of about 60° C. to about 300° C. Melting points lower than about 60° C. lead to direct thermal imaging members that are unstable to temperatures occasionally encountered during handling of the members before or after imaging, while melting temperatures above about 300° C. render the compounds difficult to colorize to a full density with a conventional thermal print head. It should be noted, however, that there are uses for certain compounds that do not require the use of thermal print heads (for example, laser imaging).

To form a preferred direct thermal imaging system, the crystalline, colorless form of the compounds is made into a dispersion in a solvent in which the compound is insoluble or only sparingly soluble, by any of the methods known in the art for forming dispersions. Such methods include grinding, attriting, etc. The particular solvent chosen will depend upon the particular crystalline material. Solvents that may be used include water, organic solvents such as hydrocarbons, esters, alcohols, ketones, nitriles, and organic halide solvents such as chlorinated and fluorinated hydrocarbons. The dispersed crystalline material may be combined with a binder, which may be polymeric. Suitable binders include water-soluble polymers such as poly(vinyl alcohol), poly(vinylpyrrolidinone) and cellulose derivatives, water-dispersed latices such as styrene/butadiene or poly(urethane) derivatives, or alternatively hydrocarbon-soluble polymers such as polyethylene, polypropylene, copolymers of ethylene and norbornene, and polystyrene. This list is not intended to be exhaustive, but is merely intended to indicate the breadth of choice available for the polymeric binder. The binder may be dissolved or dispersed in the solvent.

Following preparation of the dispersion of the compound of the present invention, and optional addition of a polymeric binder, the resultant fluid is coated onto a substrate using any of the techniques well-known in the coating art. These include slot, gravure, Mayer rod, roll, cascade, spray, and curtain coating techniques. The image-forming layer so formed is optionally overcoated with a protective layer or layers.

Where materials of the present invention are used to prepare an imaging member of the type described in U.S. Pat. No. 6,801,233 B2 the process described above is followed for each of the imaging layers. Successive layers may be coated sequentially, in tandem, or in a combination of sequential and tandem coatings.

A particularly preferred thermal imaging member according to the present invention is constructed as follows.

The substrate is a filled, white poly(ethylene terephthalate) base of thickness about 75 microns, Melinex 339, available from Dupont Teijin Films, Hopewell, Va.

A first layer deposited on the substrate is an optional oxygen barrier layer composed of a fully hydrolyzed poly (vinyl alcohol), for example, Celvol 325, available from Celanese, Dallas, Tex. (96.7% by weight), glyoxal (a crosslinker, 3% by weight) and Zonyl FSN (a coating aid, available from Dupont, Wilmington, Del., 0.3% by weight). This layer, when present, has a coverage of about 1.0 g/m$^2$.

Deposited either directly onto the substrate, or onto the optional oxygen barrier layer, is a cyan image-forming layer composed of a cyan color-former having melting point 210° C., of the type disclosed in the aforementioned U.S. Pat. No. 7,008,759 (1 part by weight), diphenyl sulfone (a thermal solvent having melting point 125° C., coated as an aqueous dispersion of crystals having average particle size under 1 micron, 3.4 parts by weight), Lowinox WSP (a phenolic antioxidant, available from Great Lakes Chemical Co., West Lafayette, Ind., coated as an aqueous dispersion of crystals having average particle size under 1 micron, 0.75 parts by weight), Chinox 1790 (a second phenolic antioxidant, available from Chitec Chemical, Taiwan, coated as an aqueous dispersion of crystals having average particle size under 1 micron, 1 part by weight), poly(vinyl alcohol) (a binder, Celvol 205, available from Celanese, Dallas, Tex., 2.7 parts by weight), glyoxal (0.084 parts by weight) and Zonyl FSN (0.048 parts by weight). This layer has a coverage of about 2.5 g/m$^2$.

Deposited onto the cyan color-forming layer is a barrier layer that contains a fluorescent brightener. This layer is composed of a fully hydrolyzed poly(vinyl alcohol), for example, the abovementioned Celvol 325, available from Celanese, Dallas, Tex. (3.75 parts by weight), glyoxal (0.08 parts by weight), Leucophor BCF P115 (a fluorescent brightener, available from Clariant Corp., Charlotte, N.C., 0.5 parts by weight), boric acid (0.38 parts by weight) and Zonyl FSN (0.05 parts by weight). This layer has a coverage of about 1.5 g/m$^2$.

Deposited on the barrier layer is a thermally-insulating interlayer composed of Glascol C-44 (a latex available from Ciba Specialty Chemicals Corporation, Tarrytown, N.Y., 18 parts by weight), Joncryl 1601 (a latex available from Johnson Polymer, Sturtevant, Wis., 12 parts by weight) and Zonyl FSN (0.02 parts by weight). This layer has a coverage of about 13 g/m$^2$.

Deposited on the thermally-insulating interlayer is a barrier layer composed of a fully hydrolyzed poly(vinyl alcohol), for example, the abovementioned Celvol 325, available from Celanese, Dallas, Tex. (2.47 parts by weight), glyoxal (0.07 parts by weight), boric acid (0.25 parts by weight) and Zonyl FSN (0.06 parts by weight). This layer has a coverage of about 1.0 g/m$^2$.

Deposited on the barrier layer is a magenta color-forming layer, composed of a magenta color-former of the present invention, preferably Dye IV, having a melting point of 152° C.; a phenolic antioxidant (Anox 29, having melting point 161-164° C., available from Great Lakes Chemical Co., West Lafayette, Ind., coated as an aqueous dispersion of crystals having average particle size under 1 micron, 3.58 parts by weight), Lowinox CA22 (a second phenolic antioxidant, available from Great Lakes Chemical Co., West Lafayette, Ind., coated as an aqueous dispersion of crystals having average particle size under 1 micron, 0.72 parts by weight), poly(vinyl alcohol) (a binder, Celvol 205, available from Celanese, Dallas, Tex., 2 parts by weight), the potassium salt of Carboset 325 (an acrylic copolymer, available from Noveon, Cleveland, Ohio, 1 part by weight) glyoxal (0.06 parts by weight) and Zonyl FSN (0.06 parts by weight). This layer has a coverage of about 2.7 g/m$^2$.

Deposited on the magenta color-forming layer is a barrier layer composed of a fully hydrolyzed poly(vinyl alcohol), for example, the abovementioned Celvol 325, available from Celanese, Dallas, Tex. (2.47 parts by weight), glyoxal (0.07 parts by weight), boric acid (0.25 parts by weight) and Zonyl FSN (0.06 parts by weight). This layer has a coverage of about 1.0 g/m$^2$.

Deposited on the barrier layer is a second thermally-insulating interlayer composed of Glascol C-44 (1 part by weight), Joncryl 1601 (a latex available from Johnson Polymer, 0.67 parts by weight) and Zonyl FSN (0.004 parts by weight). This layer has a coverage of about 2.5 g/m$^2$.

Deposited on the second interlayer is a barrier layer composed of a fully hydrolyzed poly(vinyl alcohol), for example, the abovementioned Celvol 325, available from Celanese, Dallas, Tex. (1 part by weight), glyoxal (0.03 parts by weight), boric acid (0.1 parts by weight) and Zonyl FSN (0.037 parts by weight). This layer has a coverage of about 0.5 g/m$^2$.

Deposited on the barrier layer is a yellow color-forming layer composed of Dye XI (having melting point 202-203° C.) described in U.S. patent application Ser. No. 10/789,566, filed Feb. 27, 2004, United States Patent Application Publication No. US2004/0204317 A1 (4.57 parts by weight), poly(vinyl alcohol) (a binder, Celvol 540, available from Celanese, Dallas, Tex., 1.98 parts by weight), a colloidal silica (Snowtex 0-40, available from Nissan Chemical Industries, Ltd Tokyo, Japan, 0.1 parts by weight), glyoxal (0.06 parts by weight) and Zonyl FSN (0.017 parts by weight). This layer has a coverage of about 1.6 g/m$^2$.

Deposited on the yellow color-forming layer is a barrier layer composed of a fully hydrolyzed poly(vinyl alcohol), for example, the abovementioned Celvol 325, available from Celanese, Dallas, Tex. (1 part by weight), glyoxal (0.03 parts by weight), boric acid (0.1 parts by weight) and Zonyl FSN (0.037 parts by weight). This layer has a coverage of about 0.5 g/m$^2$.

Deposited on the barrier layer is an ultra-violet blocking layer composed of a nanoparticulate grade of titanium dioxide (MS-7, available from Kobo Products Inc., South Plainfield, N.J., 1 part by weight), poly(vinyl alcohol) (a binder, Elvanol 40-16, available from DuPont, Wilmington, Del., 0.4 parts by weight), Curesan 199 (a crosslinker, available from BASF Corp., Appleton, Wis., 0.16 parts by weight) and Zonyl FSN (0.027 parts by weight). This layer has a coverage of about 1.56 g/m$^2$.

Deposited on the ultra-violet blocking layer is an overcoat composed of a latex (XK-101, available from NeoResins, Inc., Wilmington, Mass., 1 part by weight), a styrene/maleic acid copolymer (SMA 17352H, available from Sartomer Company, Wilmington, Pa., 0.17 parts by weight), a crosslinker (Bayhydur VPLS 2336, available from BayerMaterialScience, Pittsburgh, Pa., 1 part by weight), zinc stearate (Hidorin F-115P, available from Cytech Products Inc., Elizabethtown, Ky., 0.66 parts by weight) and Zonyl FSN (0.04 parts by weight). This layer has a coverage of about 0.75 g/m$^2$.

Optimal conditions for printing a yellow image using the preferred thermal imaging member described above are as follows.

Thermal printing head parameters:
Pixels per inch: 300
Resistor size: 2×(31.5×120) microns (split resistor)
Resistance: 3000 Ohm
Glaze Thickness: 110 microns
Pressure: 3 lb/linear inch
Dot pattern: Slanted grid.

The yellow color-forming layer is printed as shown in the table below. The line cycle time is divided into individual pulses of 75% duty cycle. The thermal imaging member is preheated by contact with the thermal printing head glaze at the heat sink temperature over a distance of about 0.3 mm.

|  | Yellow printing |
|---|---|
| Heat sink temperature | 25° C. |
| Dpi (transport direction) | 300 |
| Voltage | 38 |
| Line speed | 6 inch/sec |
| Pulse interval | 12.5 microsec |
| # pulses used | 8-17 |

Optimal conditions for printing a magenta image using the preferred thermal imaging member described above are as follows. Thermal printing head parameters:
Pixels per inch: 300
Resistor size: 2×(31.5×120) microns (split resistor)
Resistance: 3000 Ohm
Glaze Thickness: 200 microns
Pressure: 3 lb/linear inch
Dot pattern: Slanted grid.

The magenta color-forming layer is printed as shown in the table below. The line cycle time is divided into individual pulses of 7.14% duty cycle. The thermal imaging member is preheated by contact with the thermal printing head glaze at the heat sink temperature over a distance of about 0.3 mm.

|  | Magenta printing |
|---|---|
| Heat sink temperature | 30° C. |
| Dpi (transport direction) | 300 |
| Voltage | 38 |
| Line speed | 0.75 inch/sec |
| Pulse interval | 131 microsec |
| # pulses used | 20-30 |

Optimal conditions for printing a cyan image using the preferred thermal imaging member described above are as follows. Thermal printing head parameters:
Pixels per inch: 300
Resistor size: 2×(31.5×180) microns (split resistor)

Resistance: 3000 Ohm
Glaze Thickness: 200 microns
Pressure: 3 lb/linear inch
Dot pattern: Slanted grid.

The cyan color-forming layer is printed as shown in the table below. The line cycle time is divided into individual pulses of about 4.5% duty cycle. The thermal imaging member is preheated by contact with the thermal printing head glaze at the heat sink temperature over a distance of about 0.3 mm.

|  | Cyan printing |
| --- | --- |
| Heat sink temperature | 50° C. |
| Dpi (transport direction) | 300 |
| Voltage | 38 |
| Line speed | 0.2 inch/sec |
| Pulse interval | 280 microsec |
| # pulses used | 33-42 |

EXAMPLES

The invention will now be described further in detail with respect to specific embodiments by way of examples, it being understood that these are intended to be illustrative only and the invention is not limited to the materials, amounts, procedures and process parameters, etc. recited therein. All parts and percentages recited are by weight unless otherwise specified.

Example I

Synthesis of N-acetyl-N-octylaniline

1-Octylbromide (39 mL, 224 mmol, 1.12 eq) was added dropwise to a mixture of acetanilide (27 g, 200 mmol, 1 eq) in dimethylsulfoxide (130 mL), containing potassium hydroxide pellets (18.87 g, 300 mmol, 1.5 eq), at room temperature. After all the octyl bromide was added the reaction mixture was heated to 50-55° C. for 1.5 hours. The reaction mixture was cooled and poured into water (1 L), stirred for 45 minutes and extracted with hexanes (3×400 mL). The hexane extracts were combined, dried over sodium sulfate and evaporated to give 48.4 g (196 mmol, 98%) of colorless oil. The product was identified by NMR spectroscopy and mass spectrometry and was used without further purification.

Synthesis of N-octylaniline

To N-acetyl-N-octylaniline (48.4 g, 196 mmol) there was added 4N hydrochloric acid (100 mL) and the mixture heated to 100-110° C. and stirred at this temperature for 4 days. The reaction mixture was cooled to ambient temperature, diluted with water (100 mL), and hexanes (200 mL). The pH of the reaction mixture was brought to pH 14 by addition of 45% potassium hydroxide with cooling by an ice bath. The layers were separated and the aqueous layer washed with hexanes (100 mL). The combined organic layers were dried over sodium sulfate and concentrated by rotary evaporation to give the desired product as a light brown oil (40 g, 195 mmol, 99%). The product was identified by NMR spectroscopy and mass spectrometry and in general was used without further purification. Analytically pure product was obtained by distillation at reduced pressure: by 145-150° C. (0.5 mm).

Synthesis of 5,6-dichlorofluorescein

To a 5 L 3-neck flask fitted with a mechanical stirrer and a thermometer was added 4,5-dichlorophthalic acid (502 g, 2.13 mol) and methanesulfonic acid (2 L). The mixture was stirred at 90° C. for one hour. The mixture was cooled to 80° C. and resorcinol (470 g, 4.27 mol) was added all at once. The dark mixture was heated at 105° C. for one hour. The warm mixture was poured into a stirred mixture of ice (6 kg) and water (5 L). The mixture was stirred for 30 minutes and filtered. The filter cake was washed with water (3×500 mL). The wet filter cake was stirred with propyl acetate (2 L) and filtered again. The wet cake was dried to a constant weight and placed in the original reaction vessel. Propyl acetate (2 L) was added and the stirred mixture was heated to 90° C. and allowed to cool to room temperature and filtered. The filter cake was washed with acetone (0.4 L) and hexane (0.4 L). The mustard yellow solid was dried to a constant weight in the vacuum oven to afford 930 g (109% yield). The product was identified by NMR spectroscopy and mass spectrometry.

Synthesis of 3',6',5,6-tetrachlorofluoran

To a 5 L 3-necked fitted with a mechanical stirrer, a thermometer, and a dropping funnel was added dichlorofluorescein (930 g, ca. 2.13 mol), sulfolane (2.4 L), and dimethylformamide (152 mL, 1.9 moles). The stirred mixture was warmed to 90° C. and phosphorus oxychloride (0.72 L) was added dropwise over one hour while keeping the temperature between 90 and 95° C. After the addition was complete, the mixture was kept at the same temperature for one hour and poured into acetone:water (2:1,11 L). The mixture was stirred for one hour and filtered. The filter cake was washed with acetone: water (2 L) and dried in a vacuum oven to a constant weight. A beige solid was obtained. (805 g, 1.84 mol, 86% overall yield for two steps). The product was identified by NMR spectroscopy and mass spectrometry.

Synthesis of 3'-chloro-6'-tetrahydroquinolinofluoran

A mixture of dichlorofluoran (3.7 g, 0.01 mol), aluminum chloride (9 g, 0.07 mol) and tetrahydroquinoline (2.6 g, 0.02 moles) in sulfolane (25 ml) was held at 150° C. for 18 hours. The reaction mixture was quenched into 100 ml of water. The solid was filtered off, washed with water and dried. The product was purified on silica gel using 2% methanol in methylene chloride to yield 3'-chloro-6'-tetrahydroquinolinofluoran (250 mg, 0.54 mmol, 5.4%). The product was identified by NMR spectroscopy and mass spectrometry.

Synthesis of 3'-chloro-6'-(N-ethylaniline)-5,6-dichlorofluoran

A three-necked flask equipped with mechanic stirrer and thermometer was charged with 3',6',5,6-tetrachlorofluoran (8.8 g, 20 mmol) and 40 mL of sulfolane. Aluminum chloride (11.0 g, 80 mmol) was added to the mixture in portions with stirring. At 60° C., N-ethylaniline (6.05 g, 50 mmol, 2.5 eq) was added dropwise over 15 minutes. The reaction was monitored by HPLC. After the starting materials were consumed, the reaction mixture was cooled and poured into 2 N HCl (500 mL). The precipitated solid was filtered, washed and air-dried. The free base was obtained by dissolving the salt in DMF, followed by pouring into ammonia hydroxide solution. The product was washed with water and dried. (Yield: 9.36 g, 17 mmol, 85%) The product was identified by NMR spectroscopy and mass spectrometry.

Synthesis of 3'-N-butylanilino-6'-chlorofluoran

3',6'-dichlorofluoran (15.0 g, 40.6 mmol) was taken up in sulfolane (80 mL), heated to 60° C. and aluminum chloride (21.0 g, 157.9 mmol, 3.9 eq.) was added in one portion. N-Butylaniline (15 mL, 98.3 mmol, 2.4 eq.) was then added dropwise over 5 minutes and the reaction was heated at 80° C. for 1 hour. The reaction mixture was poured into 3N hydrochloric acid and ice. The resulting precipitate was filtered, washed with water and dried overnight to afford the crude 3'-N-butylanilino-6'-chlorofluoran (18.9 g, 39.2 mmol, 96%) which was used as such. The product was identified by NMR spectroscopy and mass spectrometry.

Synthesis of 3'-chloro-6'-(N-octylaniline)-5,6-dichlorofluoran

To a solution of 3',6',5,6-tetrachlorofluorescein (8.8 g, 0.02 mol) in sulfolane (40 mL) was added aluminum chloride (11:0 g, 0.08 mol) in portions with stirring. This was followed by the addition of N-octylaniline (4.4 g, 0.022 mol) at 50° C. over 5 minutes. After 30 minutes, triethylamine (6.0 g, 0.06 mol) was added dropwise over 10 minutes. After the starting materials were consumed (HPLC) the reaction mixture was cooled and poured into 2 N HCl (500 mL). The precipitated solid was filtered, washed and air-dried. The free base product was obtained by dissolving the salt in DMF, followed by pouring into ammonium hydroxide solution. The product was identified by NMR spectroscopy and mass spectrometry.

Synthesis of 3'-chloro-6'-(2-methylanilino)-fluoran

To a suspension of 3',6'-dichlorofluoran (30 g, 81 mmol) in sulfolane (120 mL) was added AlCl$_3$ (3.0 eq., 244 mmol, 32.4 g) and the mixture was warmed to 60° C. Toluidine (1.1 eq., 89.4 mmol 9.6 g) was added and the temperature of the orange solution was maintained at 60° C. for 10 minutes. Neat triethylamine (1.05 eq., 85.4 mmol, 8.64 g was added dropwise with stirring over a period of 10 minutes. After stirring at 70° C. open to air for 4 hours, the solution was poured into a vigorously stirred beaker of water (1 L). The resulting suspension was filtered, and the collected solids were dissolved in ethyl acetate (500 mL). The organic extracts were dried over sodium sulfate and adsorbed on silica (~100 g). The product was purified by silica gel column chromatography (1:1 Hexane/EtOAc) to yield an orange solid. The product was identified by NMR spectroscopy and mass spectrometry.

Example II

Synthesis of Dye I

A mixture of 3'-chloro-6'-tetrahydroquinolinofluoran (100 mg, 0.2 mmol), decylamine (100 mg, 0.6 mmol), and zinc chloride (100 mg, 0.7 mmol) in sulfolane (3 mL) was held at 150° C. for 3 hours. The reaction mixture was quenched into 10 ml of water. The solid was filtered off, washed with water and dried. The product was purified by silica gel chromatography using 2% methanol in methylene chloride to yield 3'N-decylamino-6-tetrahydroquinoline fluoran as an off-white solid (42 mg, 0.07 mmol, 35%). The product was identified by NMR spectroscopy and mass spectrometry.

Example III

Synthesis of Dye VII

To a solution of 3'-N-ethylanilino-6'-chlorofluoran (1.82 g, 4 mmol) in 12 ml of sulfolane was added zinc chloride (1.63 g, 12 mmol), zinc oxide (0.32, 4 mmol) and cyclohexylamine (1.6 g, 16 mmol). The reaction mixture was heated to 140° C. under stirring overnight (18 hours). After being cooled to room temperature, the reaction mixture was poured into water (100 mL) and the precipitated crude product was obtained by filtration, dried in air and dissolved in methylene chloride (50 mL). After removing insoluble solids by filtration, the resulting filtrate was subjected to chromatography (silica gel, hexane/ethyl acetate as eluent). The isolated oil product was recrystalized in a mixed solution of hexane and ethyl acetate to give 0.7 g of light pink crystals, m.p.: 212-214° C.). The product was identified by NMR spectroscopy and mass spectrometry.

Example IV

Synthesis of Dye VIII

To a solution of 3'-N-ethylanilino-6'-chlorofluoran (1.82 g, 4 mmol) in 12 ml of sulfolane was added zinc chloride (1.63 g, 12 mmol), zinc oxide (0.32, 4 mmol) and adamantylamine (2.4 g, 16 mmol). The reaction mixture was heated to 150° C. under stirring overnight. After being cooled to room temperature, the reaction mixture was poured into 100 ml water, the precipitated crude product obtained by filtration and dried in vacuum and then dissolved in methylene chloride. After removal of insoluble solid, the resulting filtrate was concentrated to the appropriate volume for being loaded on chromatography (silica gel, hexane/ethyl acetate as eluent). The isolated oil was converted into light pink crystals in a mixed solution of hexane and ethyl acetate under stirring (0.55 g, m.p.: 240-242° C.). The product was identified by NMR spectroscopy and mass spectrometry.

Example V

Synthesis of Dye IX

To a solution of 3'-chloro-6'-(N-butylaniline)-5,6-dichlorofluoran (2.2 g, 4 mmol) in 12 ml of sulfolane was added zinc chloride (1.63 g, 12 mmol), zinc oxide (0.32, 4 mmol) and cyclohexylamine (1.6 g, 16 mmol). The reaction mixture was heated to 140° C. under stirring overnight. After being cooled to room temperature, the reaction mixture was poured into water (100 mL) and the precipitated crude product was obtained by filtration, subjected to chromatography (silica gel, hexane/ethyl acetate as eluent) using methylene chloride as solvent for loading. The isolated oil product was recrystallized in hexane mixed with 30% of ethyl acetate to give 0.56 g of light pink crystals, m.p.: 193-195° C. The product was identified by NMR spectroscopy and mass spectrometry.

Example VI

Synthesis of Dye X

To a solution of 3'-chloro-6'-(N-butylaniline)-5,6-dichlorofluoran (2.2 g, 4 mmol) in 12 ml of sulfolane was added zinc chloride (1.63 g, 12 mmol), zinc oxide (0.32, 4 mmol) and adamantylamine (2.4 g, 16 mmol). The reaction mixture was heated to 150° C. under stirring overnight. After being cooled to room temperature, the reaction mixture was poured into water (100 mL) and the precipitated crude product obtained by filtration, dried in vacuum and directly subjected to chromatography (silica gel, hexane/ethyl acetate as eluent) with methylene chloride as loading solvent, ignoring insoluble solid. The isolated oil product was transformed into light pink crystals by recrystallization from a mixed solution of hexane and ethyl acetate (0.45 g, m.p.: 252-254° C.). The product was identified by NMR spectroscopy and mass spectrometry.

Example VII

Synthesis of Dye XI

To a solution of 3'-chloro-6'-(N-octylaniline)-5,6-dichlorofluoran (1.82 g, 3 mmol) in 12 ml of sulfolane was added zinc chloride (1.30 g, 9 mmol), zinc oxide (0.25 g, 3 mmol) and cyclohexylamine (1.2 g, 12 mmol). The reaction mixture was heated to 140° C. under stirring overnight. After being cooled to room temperature, the reaction mixture was poured into 2 N HCl (100 mL), the precipitated crude product obtained by filtration, dried in vacuum and dissolved in DMF (20 mL). The mixed DMF solution was poured into 10% ammonium hydroxide (100 mL). The resulting red crude product was subjected to chromatography (silica gel, hexane/ethyl acetate as eluent) for further purification. The isolated oil product was converted into light pink crystals by recrystallization from a mixed solution of hexane and ethyl acetate (0.77 g, m.p.: 162-164° C.). The product was identified by NMR spectroscopy and mass spectrometry.

Example VIII

Synthesis of Dye XII

To a solution of 3'-chloro-6'-(2-methylanilino)-fluoran (3 g, 7 mmol) in sulfolane (10 mL) was added lutidine (1.1 eq., 7.7 mmol, 0.83 g) followed by ZnO (0.8 eq., 5.6 mmol, 456 mg) and ZnCl$_2$ (3.0 eq., 21 mmol, 2.86 g). The solution was warmed to 100° C. and pyrrolidine (1.5 eq., 10.5 mmol, 747 mg) was added. After 1 hour the red solution was poured into water (500 mL), filtered and the collected solids were dissolved in ethyl acetate (500 mL). The organic extracts were washed with 0.5 N KOH (100 mL) and dried with magnesium sulfate. The solvent was removed under reduced pressure and the product purified by silica gel column chromatography (1:1 Hexanes/EtOAc→EtOAc gradient) to yield ID747 (2.49 g, 5.25 mmol, 75%). The purified product was crystallized from acetone/hexanes to yield 1.5 g of pink powder. The product was identified by NMR spectroscopy and mass spectrometry.

Example IX

Synthesis of Dye XIII

To a suspension of 3',6'-dichlorofluoran (184.5 gm; 0.5 mol) in sulfolane (800 mL) was added AlCl$_3$ (3.0 eq., 200 g; 1.5 mol) and the mixture was warmed to 60° C. followed by the addition of. 4-fluoro-2-methylaniline (68.8 gm; 0.55 mol). The temperature of the orange solution was maintained at 80° C. for 10 minutes. Neat triethylamine (1.21 eq., 82.5 mL; 0.605 mol) was added drop wise with stirring over a period of 10 minutes. After stirring at 80° C. for four hours the completion of the reaction was followed by TLC of an aliquot (Ethyl acetate:hexanes, 1:4).

Lutidine (2.2 eq., 127.9 ml; 1.1 mol) and pyrrolidine (39.10 g; 0.55 mol) were added to the warm reaction solution. The reaction mixture was stirred at 80° C. overnight. The reaction did not go to completion based on TLC even when extra lutidine and pyrrolidine were added. The reaction mixture was cooled and then poured into ice/water (1.0 L) and stirred for 30 minutes and filtered. The filtrate was washed with of water (1.0 L).

The resulting paste was dissolved in dichloromethane (2.0 L) and washed with water. The organic layer was separated, dried over sodium sulfate and evaporated. The crude dye was purified by silica gel chromatography through a short plug. A gradient of ethyl acetate/hexane was used as eluent. The fractions containing pure product were combined, evaporated and recrystallized from acetone to give colorless crystals of Dye XIII (83 g; 33.7%). DSC=283 C. The product was identified by NMR spectroscopy and mass spectrometry.

Example X

Synthesis of Dye XIV

To a suspension of 3',6'-dichlorofluoran (9.225 g, 25 mmol) in sulfolane (50 mL) was added AlCl$_3$ (3.0 eq., 10 g; 75 mmol) and the mixture was warmed to 60° C. followed by the addition of 4-fluoro-toluidine (3.44 g; 27.25 mmol). The temperature of the orange solution was maintained at 80° C. for 10 minutes. Neat triethylamine (1.1 eq., 3.75 ml.; 27.25 mmol) was added dropwise with stirring over a period of 10 minutes. The reaction was stirred at 80° C. for 4 hours. The completion of the reaction was followed by TLC of an aliquot. (Ethyl acetate:hexane:: 1:4).

Lutidine (2.0 eq., 7.85 ml; 50 mmol) and 2-methyl-pyrrolidine (2.32 g; 27.25 mmol) were added to the warm reaction solution. The reaction mixture was stirred at 80° C. overnight. The reaction did not go to completion based on TLC even when extra lutidine and pyrrolidine were added. The reaction mixture was cooled and then poured into ice/water (500 ml), stirred for 30 min., filtered and washed with water (100 mL).

The resulting paste was dissolved in 400 ml of dichloromethane and washed with water. The organic layer was separated, dried over sodium sulfate and evaporated. The crude dye was purified by silica gel chromatography. A gradient of ethyl acetate/hexane was used as eluent. The fractions containing pure product were combined, evaporated and recrystallized from a mixture of acetone/hexanes to give colorless crystals of Dye XIV (4.12 g; 32.54%). The product was identified by NMR spectroscopy and mass spectrometry.

Example XI

This example illustrates a thermal imaging method according to the invention.

The following materials were used in this example:

Celvol 205, a grade of poly(vinyl alcohol) available from Celanese Corporation, Dallas, Tex.;

Celvol 325, a grade of poly(vinyl alcohol) available from Celanese Corporation, Dallas, Tex.;

Celvol 540, a grade of poly(vinyl alcohol) available from Celanese Corporation, Dallas, Tex.;

Elvanol 40-16, a grade of poly(vinyl alcohol) available from DuPont Company Americas, Wilmington, Del.;

Neocryl XK-101, available from DSM NeoResins, Wilmington, Mass.;

NeoCryl A-639, available from DSM NeoResins, Wilmington, Mass.;

Ucar 451, a styrene-acrylic latex available from Dow Chemical, Cary, N.C.;

Bayhydur VP LS2336, available from Bayer Material Science LLC, Pittsburgh, Pa.;

Glascol C44, a polyacrylamide available from Ciba Specialty Chemicals, Tarrytown, N.J.;

Joncryl J1601, a styrene-acrylic emulsion from Johnson Polymer, Sturtevant, Wis.:

Leucophor BCF P115 (a fluorescent brightener, available from Clariant Corp., Charlotte, N.C.);

Titanium dioxide, MS-7, available from Kobo Products Inc., South Plainfield, N.J.;

Titanium dioxide white pigment TiPure® R900, available from DuPont, Wilmington, Del.;

Zonyl FSN, a surfactant, available from DuPont Corporation, Wilmington, Del.;

Diphenylsulfone available from Seal Sands Chemical, Seal Sands, UK;

2,2'-Methylenebis(6-tert-butyl-4-methylphenol) available from Great Lakes Chemical, West Lafayette, Ind.;

2,2'-Methylenebis(6-tert-Butyl-4-Ethyl-Phenol) available from Great Lakes Chemical, West Lafayette, Ind.;

2,2'-Ethylidenebis(4,6-di-tert-butylphenol) Available from Great Lakes Chemical, West Lafayette, Ind.;

Bis[2-hydroxy-5-methyl-3-(1-methylcyclohexyl)phenyl]-methane available from Great Lakes Chemical, West Lafayette, Ind.;

1,3,5-Tris(2,6-dimethyl-3-hydroxy-4-tert-butylbenzyl) isocyanurate available from Great Lakes Chemical, West Lafayette, Ind.;

Pluronic 25R4, a surfactant available from BASF, Florham Park, N.J.;

Surfynol CT-111, Surfynol CT-131 and Surfynol GA, surfactants available from Air Products and Chemicals, Inc. Allentown, Pa.;

Tamol 731, a surfactant available from Rohm and Haas Co. Philadelphia, Pa.;

Triton X-100, a surfactant available from The Dow Chemical Company, Midland, Mich.;

Hidorin F-115P, a grade of zinc stearate available from Cytech Products Inc., Elizabethtown, Ky.;

Nalco 30V-25, a silica dispersion available from ONDEO Nalco Company, Chicago, Ill.;

Snowtex a colloidal silica available from Nissan Chemical-America Corporation, Houston, Tex.;

Melinex X967, a transparent poly(ethylene terephthalate) film base of approximately 5 mils in thickness, available from DuPont Teijin Films, Hopewell, Va.

Yellow Color Former: Dye VI described in U.S. patent application Ser. No. 10/789,566, filed Feb. 27, 2004, United States Patent Application Publication No. US2004/0204317 A1;

Magenta Color Former: Dye IV of the present application;

Cyan Color Former: A dye, 3'-(2,3-dihydro-1H-indol-1-yl)-4,5,6,7-tetrafluoro-6'-[(4-methoxy-2-methylphenyl) amino]-Spiro[isobenzofuran-1(3H),9'-[9H]xanthen]-3-one, made according to the procedures described in United States Patent Application Publication No. US2004/0191668.

The imaging member was prepared by successive coatings applied to a substrate, Melinex X967, as follows:

A cyan image-forming layer was applied as follows:

Cyan Color Former (77.68 g, melting point 205 C) was dispersed in a mixture of Pluronic 25R4 (2.06 g), Surfynol CT-131 (1.59 g of a 52% aqueous solution), Triton X100 (2.06 g) methyl acetate (48.16 g) and water (143.4 g), using an attritor equipped with glass beads, stirred for 18 hours at room temperature. The dispersion was then diluted with water (275 g) so that the total solid content of the resulting dispersion was 15%.

Thermal solvent dispersion A: diphenylsulfone (212.72 g) was dispersed in a mixture comprising Tamol 731 (198 g of a 6.30% solution in water, adjusted with sulfuric acid to a pH of 5), Celvol 205 (125.5 g of a 20% solution in water) and water (213.8 g), using an attritor equipped with glass beads, and stirred for 18 hours at room temperature. The resulting dispersion was then diluted with water (500 g) so that the total solid content was 20%.

Thermal Solvent Dispersion B: Bis[2-hydroxy-5-methyl-3-(1-methylcyclohexyl)phenyl]-methane (360 g) was dispersed in a mixture comprising Surfynol CT-151 (22.5 g of a 40% solution in water), Surfynol GA (25.7 g of a 70% solution in water) and water (1392 g), using an attritor equipped with glass beads, stirred for 18 hours at room temperature. The total solid content of the resulting dispersion was 20%.

Thermal Solvent Dispersion C: 1,3,5-Tris(2,6-dimethyl-3-hydroxy-4-tert-butylbenzyl) isocyanurate (518.6 g) was dispersed in a mixture comprising sodium laurel sulfate (16.2 g), Surfynol CT-111 (5.1 g) and water (1260 g), using an attritor equipped with glass beads, and stirred for 18 hours at room temperature. The total solid content of the resulting dispersion was 30%.

The above dispersions were combined with water and the materials listed in the table below to make the coating fluid for the cyan dye-forming layer in the proportions stated. The coating composition thus prepared was coated onto Melinex X967 to give a layer with a dried thickness of 2 microns.

| Ingredient | % solids in coating fluid |
| --- | --- |
| Cyan Dye Dispersion | 0.740 |
| Thermal Solvent Dispersion A | 2.58 |
| Thermal Solvent Dispersion B | 0.55 |
| Thermal Solvent Dispersion C | 0.740 |
| Celvol 205 | 3.14 |
| Zonyl FSN | 0.020 |
| Glyoxal | 0.090 |

A barrier layer was next applied as follows:

A fluid was prepared from the materials listed in the table below by mixing in water and coated on top of the cyan dye-forming layer to a dried thickness of 2 microns.

| Ingredient | % solids in coating fluid |
| --- | --- |
| Celvol 125 | 3.75 |
| Boric Acid | 0.375 |
| Leucophor 115 | 0.500 |
| Glyoxal | 0.037 |
| Zonyl FSN | 0.047 |

An interlayer was next applied as follows:

Water was combined with the materials listed in the table below to provide a coating fluid, which was coated onto the barrier layer for a dried thickness of 13.5 microns.

| Ingredient | % solids in coating fluid |
| --- | --- |
| Joncryl 1601 | 12.0 |
| Glascol C44 | 18.0 |
| Zonyl FSN | 0.020 |

A yellow image-forming layer was applied as follows:

Yellow Color Former (114 g) was dispersed in a mixture comprising Tamol 681(173.4 g of a 3.46% solution in water), methyl acetate (56 g) and water (56.6 g), using an attritor equipped with glass beads, stirred for 18 hours at room temperature. The total solid content of the resulting dispersion was 30%.

The above dispersion was combined with water and the materials listed in the table below to make the coating fluid for the yellow dye-forming layer in proportions stated. The coating composition thus prepared was coated onto the interlayer prepared above for a dried thickness of 2 microns.

| Ingredients | % solids in coating fluid |
| --- | --- |
| Yellow dye dispersion | 3.50 |
| Celvol 540 | 1.50 |
| Snowtex 0-40 | 0.075 |
| Zonyl FSN | 0.050 |
| Glyoxal | 0.045 |

A second barrier layer was applied as follows:

Water was combined with the materials listed in the table below to provide a coating fluid, which was coated onto the yellow color-forming layer to give a dried thickness of 1.5 microns.

| Ingredients | % solids in coating fluid |
| --- | --- |
| Celvol 325 | 3.25 |
| Zonyl FSN | 0.046 |
| Boric Acid | 0.325 |

Next a UV absorbing layer was applied as follows:

Titanium dioxide (MS-7, 600 g) was dispersed in a mixture of styrene maleic anhydride (264.7 g of a 34% aqueous solution), Zonyl FSN (1.20 g) and water (634.1 g) using a Meyers Mill for 18 hours followed by 12 cycles through a Dyno-Mill. The resulting dispersion was then diluted with water (200 g) to give a dispersion with total solids of 40.7%.

Water was combined with the materials listed in the table below to provide a coating fluid, which was coated onto the barrier layer above to give a dried thickness of 1.8 microns.

| Ingredients | % solids in coating fluid |
| --- | --- |
| Elvanol 4016 | 2.69 |
| Zonyl FSN | 0.090 |
| Titanium Dioxide Dispersion | 6.23% |

An overcoat was applied as follows:

Water was combined with the materials listed in the table below to provide a coating fluid, which was in-line blended with Bayhydur VP LS 2336 (50% solution in methyl acetate) coated onto the UV absorbing layer for a dried thickness of 1.5 microns.

| Ingredients | % solids in coating fluid |
| --- | --- |
| XK 101 | 1.188 |
| UCAR 451 | 1.859 |
| Zonyl FSN | 0.097 |
| Hidorin F-115P | 0.699 |
| Nalco 2327 | 1.747 |
| Bayhydur VP LS 2336 | 1.410 |

On the opposite side of the Melinex base a magenta color-forming layer was applied:

Magenta Color Former IV (79.9 g) was dispersed in a mixture comprising Surfynol CT-111 (2.76 g of a 52% solution in water), Surfynol CT-131 (3.64 g), methyl acetate (68 g) and water (270.7 g), using an attritor equipped with glass beads, stirred for 18 hours at room temperature. The total solid content of the resulting dispersion was 20%.

The above dispersion was combined with water and the materials listed in the table below to make the coating fluid for the magenta dye-forming layer in the proportions stated. The coating composition thus prepared was coated onto the Melinex X967 for a dried thickness of 2 microns.

| Ingredients | % solids in coating fluid |
| --- | --- |
| Magenta Dye Dispersion | 0.850 |
| Celvol 205 | 4.532 |
| Nalco 2327 | 2.266 |
| Thermal Solvent Dispersion A | 5.10 |
| Thermal Solvent Dispersion B | 0.640 |
| Thermal Solvent Dispersion C | 0.090 |
| Zonyl FSN | 0.020 |
| Glyoxal | 0.110 |

Next a barrier layer was applied:

A fluid was prepared from the materials listed in the table below by mixing in water and coated on top of the cyan dye-forming layer to a dried thickness of 2 microns.

| Ingredient | % solids in coating fluid |
| --- | --- |
| Celvol 325 | 3.25 |
| Boric Acid | 0.325 |
| Zonyl FSN | 0.046 |

Next a white reflecting layer was applied:

Titanium dioxide (TiPure® R-900, 272.3 kg) was dispersed in a mixture of styrene maleic anhydride 1440 H (42.1 kg of a 34% aqueous solution), BYK-012 (0.268 kg) and water (68.3 kg) using a Meyers Mill for 18 hours followed by 4 cycles through a Dyno-Mill. This process provided a dispersion of 74.9% total solids.

The above dispersion was combined with water and the ingredients shown in the table below to give a coating fluid of 39.4% total solids. This coating fluid was in-line blended with Bayhydur VP LS 2336 (50% solution in methyl acetate) and coated onto the barrier layer for a dried thickness of 20 microns.

| Ingredient | % solids in coating fluid |
| --- | --- |
| Celvol 205 | 0.848 |
| Titanium Dioxide Dispersion | 31.29 |
| Neocryl XK-101 | 7.212 |
| Zonyl FSN | .042 |

For the final coating a backcoat was applied:

Water was combined with the materials listed in the table below to provide a coating fluid, which was in-line blended with Bayhydur VP LS 2336 (50% solution in methyl acetate) coated onto the UV absorbing layer for a dried thickness of 1.5 microns.

| Ingredients | % solids in coating fluid |
| --- | --- |
| XK 101 | 0.487 |
| UCAR 451 | 2.557 |
| Zonyl FSN | 0.097 |
| Hidorin F-115P | 0.690 |
| Nalco 2327 | 1.747 |
| Bayhydur VP LS 2336 | 1.420 |

The resulting imaging member was printed using a laboratory test-bed printer equipped with two thermal heads, model KPT-163-12PAN20(Kyocera Corporation, 6 Takedatobadono-cho, Fushimi-ku, Kyoto, Japan).

The following printing parameters were used:
Printhead width: 6.0 inch
Pixels per inch: 300
Resistor size: 70×120 microns
Resistance: 2800-3200 Ohm
Pressure: 1.5-2 lb/linear inch
Dot pattern: Rectangular grid.

The yellow layer was printed from the front side with a high power/short time condition. A lower power/longer time condition was used to print the cyan layer which was also addressed from the front side. The printhead pulsing producing yellow coloration and the printhead pulsing producing cyan coloration were interleaved, and were supplied by a single print head in a single pass, so that a single print head was printing two colors synchronously.

The magenta layer was printed with a low-power, long-time condition from the backside (the side of the film base bearing the opaque TiO2 layer).

In addition to printing gradations of color for each of the three dye layers, gradations of combined pairs of the colors and of the combinations of all three colors, were printed. Table II summarizes the printing results for this imaging example.

TABLE II

|  | Dmin | Dmax |
| --- | --- | --- |
| Yellow | 0.122 | 1.15 |
| Magenta | 0.149 | 1.43 |
| Cyan | 0.159 | 1.29 |
| Black |  | 1.70 |

Although the invention has been described in detail with respect to various preferred embodiments, it is not intended to be limited thereto, but rather those skilled in the art will recognize that variations and modifications are possible which are within the spirit of the invention and the scope of the appended claims.

We claim:

1. A thermal imaging member comprising, a substrate carrying an image-forming layer which includes an amorphochromic compound represented by the formula

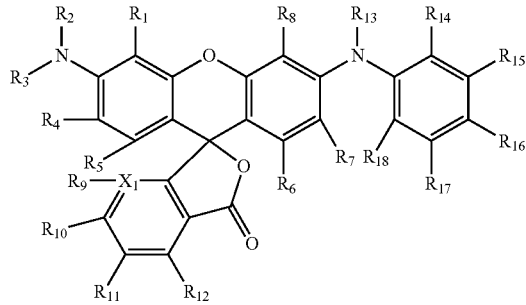

wherein:

$R_1$, $R_3$, $R_4$, $R_5$, $R_6$, $R_7$, $R_8$ and $R_{14}$ are each independently selected from the group consisting of hydrogen, alkyl, substituted alkyl, alkenyl, substituted alkenyl, heterocycloalkyl, substituted heterocycloalkyl alkoxy, substituted alkoxy, substituted carbonyl, acylamino, halogen, aryl, substituted aryl, heteroaryl and substituted heteroaryl;

$R_2$ is selected from the group consisting of hydrogen, alkyl, substituted alkyl, alkenyl, substituted alkenyl, heterocycloalkyl and substituted heterocycloalkyl; or $R_2$ and $R_3$ taken together with the nitrogen atom to which they are attached can form a substituted or unsubstituted saturated heterocyclic ring moiety;

$R_9$ is absent or selected from the group consisting of hydrogen, alkyl, substituted alkyl, alkenyl, substituted alkenyl, heterocycloalkyl, substituted heterocycloalkyl, alkoxy, substituted alkoxy, substituted carbonyl, halogen, aryl, substituted aryl, heteroaryl, substituted heteroaryl, amino, substituted amino, alkylamino, substituted alkylaino, arylamino and substituted arylamino;

$R_{10}$, $R_{11}$ and $R_{12}$ are each independently selected from the group consisting of hydrogen, alkyl, substituted alkyl, alkenyl, substituted alkenyl, heterocycloalkyl, substituted heterocycloalkyl, alkoxy, substituted alkoxy, substituted carbonyl, halogen, aryl, substituted aryl, heteroaryl, substituted heteroaryl, amino, substituted amino, alkylamino, substituted alkylamino, arylamino and substituted arylamino $R_{13}$ is selected from the group consisting of hydrogen, alkyl, substituted alkyl, alkenyl, substituted alkenyl, heterocycloalkyl and substituted heterocycloalkyl;

$R_{14}$ is selected from the group consisting of hydrogen, alkyl, substituted alkyl, alkenyl, substituted alkenyl, heterocycloalkyl and substituted heterocycloalkyl; or $R_{13}$ and $R_{14}$ taken together with the atoms to which they are attached can form a 5- or 6- membered heterocyclic ring;

$R_{15}$, $R_{16}$, $R_{17}$ and $R_{18}$ are each independently selected from the group consisting of hydrogen, alkyl, substituted alkyl, alkenyl, substituted alkenyl, heterocycloalkyl, substituted heterocycloalkyl, alkoxy, substituted alkoxy, substituted carbonyl, halogen, aryl, substituted aryl, heteroaryl, substituted heteroaryl, amino, substituted amino, alkylamino, substituted alkylamino, arylamino and substituted arylamino; and $X_1$ is carbon or nitrogen;

provided that only one of $R_2$ and $R_{13}$ is hydrogen, wherein said compound is colorless in a crystalline form.

2. The thermal imaging member as defined in claim 1 wherein said amorphochromic compound represented by formula I has a glass transition temperature of at least 50° C.

3. The thermal imaging member as defined in claim 1 wherein said image-forming layer further comprises at least one thermal solvent.

4. The thermal imaging member as defined in claim 3 wherein said thermal solvent is selected from the group consisting of diphenylsulfone, 4,4'- dimethyldiphenylsulfone, phenyl p-tolylsulfone, 4,4'-dichlorodiphenylsulfone, and mixtures thereof.

5. The thermal imaging member as defined in claim 1 wherein said image-forming layer further comprises at least one compound comprising a phenolic grouping.

6. The thermal imaging member as defined in claim 5 wherein said compound comprising a phenolic grouping is selected from the group consisting of 2,2'- methylenebis (6-tert-butyl-4-methylphenol), 2,2'-methylenebis (6-tert-Butyl-4-Ethyl-Phenol), 2,2'- ethylidenebis (4,6-di-tert-butylphenol), bis[2-hydroxy-5-methyl-3-(1-methylcyclohexyl) phenyl]-methane, 1,3,5- tris (2,6-dimethyl-3-hydroxy-4-tert-butylbenz yl) isocyanurate, 2,6-bis([3-(1,1-dimethylethyl)-2-hydroxy-5-methylphenyl]methyl]-4-methyl-phenol, 2,2'-butylidenebis[6-(1,1-dimethylethyl)-4-methyl-phenol, 2,2'-(3,5, 5-trimethylhexylidene)bis[4,6-dimethyl-phenol], 2,2'-methylenebis[4,6-bis(1,1-dimethylethyl) - phenol, 2,2'-(2-methylpropylidene)bis[4,6-dimethyl- phenol], 1,1,3-tris (2-methyl-4-hydroxy-5-t-butylphenyl)butane, tris(3,5-di-t -butyl-4- hydroxybenzyl) isocyanurate, 2,2'-thiobis(4-tert- octylphenol), and 3-tert-butyl-4-hydroxy-5-methylphenyl sulfide.

7. A thermal imaging method comprising
(a) providing an imaging member as defined in claim 1; and
(b) converting at least a portion of said amorphochromic compound to an amorphous form in an image-wise pattern whereby an image is formed.

8. The thermal imaging method as defined in claim 7 wherein step (b) comprises applying an image-wise pattern of thermal energy to said imaging member, said thermal energy being sufficient to convert at least some of said amorphochromic compound to an amorphous form.

9. The thermal imaging member of claim 1, wherein the amorphochromic compound is magenta colored in an amorphous form.

* * * * *